US 6,960,345 B2

(12) United States Patent
Moyer

(10) Patent No.: US 6,960,345 B2
(45) Date of Patent: Nov. 1, 2005

(54) ORAL VACCINIA FORMULATION

(75) Inventor: Mary Pat Moyer, San Antonio, TX (US)

(73) Assignee: Incell Corporation, LLC, San Antonio, TX (US)

( * ) Notice: Subject to any disclaimer, the term of this patent is extended or adjusted under 35 U.S.C. 154(b) by 0 days.

(21) Appl. No.: 10/379,572

(22) Filed: Mar. 6, 2003

(65) Prior Publication Data

US 2004/0175398 A1 Sep. 9, 2004

(51) Int. Cl.[7] ............................................. A61K 39/285
(52) U.S. Cl. .............................. 424/232.1; 424/199.1; 424/400
(58) Field of Search ...................... 424/199.1, 232.1, 424/400, 457, 484, 93.1, 93.2, 93.6

(56) References Cited

U.S. PATENT DOCUMENTS

| | | | | |
|---|---|---|---|---|
| 5,676,950 A | * | 10/1997 | Small et al. .............. | 424/199.1 |
| 6,090,925 A | * | 7/2000 | Woiszwillo et al. ......... | 530/410 |
| 2003/0059471 A1 | * | 3/2003 | Compton et al. ........... | 424/489 |
| 2003/0059474 A1 | * | 3/2003 | Scott et al. ................. | 424/491 |
| 2003/0068385 A1 | * | 4/2003 | Moyer et al. ............... | 424/523 |

FOREIGN PATENT DOCUMENTS

| WO | WO99/07869 | * | 2/1999 | ........... C12N/15/86 |
|---|---|---|---|---|

OTHER PUBLICATIONS

Wyatt et al. (PNAS 101:4590–4595, 2004).*

Earl et al. (Nature 428:182–185, 2004).*

Belyakov et al. (PNAS 100:9458–9463, 2003).*

Nechaeva (Expert Review of Vaccines 1(3):385–97, 2002).*

* cited by examiner

Primary Examiner—Mary E. Mosher
(74) Attorney, Agent, or Firm—Susan J. Friedman

(57) ABSTRACT

This invention relates to methods and systems for generating a safe and effective oral smallpox vaccine for humans using a genetically defective strain of vaccinia virus to confer immunity following oral delivery of the vaccine. This invention is one that expands on current use of vaccinia virus propagation developed for gene therapy applications, and pharmaceuticals and nutraceuticals packaging and formulation technologies. The vaccine invention can be delivered as a live virus with the ability to express viral proteins but unable to achieve complete, lytic virus replication, or it may be derived from such a virus, contain additional immunogens, or be delivered as viral antigens. Furthermore, the invention establishes innovative methods for formulation and packaging and for preclinical testing of the vaccine invention for safety, efficacy and potency with the use of human intestinal and other test cells and diagnostic test systems and kits.

25 Claims, 18 Drawing Sheets

BHK-21 Cells Growing in Culture

Figure 1:

Immunoplaque Focus Formation Assay in BHK Cells to Titer Virus

Example of ELISA Assays of Rabbit (TiterMax) Antibodies

Example of ELISA Assays of Sheep (TiterMax) Antibodies

Example of ELISA Assays of Orally Immunized Rabbit Antibodies at Early Immunization Time Compared to Pre-bleed

Example ELISA Assays of Orally Immunized Rabbit Antibodies Show Continued Antibody Production

Example of ELISA Assays of Orally Immunized Sheep Antibodies

Sheep # 2: Oral Immunization
Serum Anti-I-MVA Antibody Titer
ELISA

FIGURE 8

Example of Western Blot Assays with Rabbit Antibodies

Lane 1: MW Markers
Lane 2: Rabbit # 2, Day 0 serum against I-MVA
Lane 3: Rabbit # 2, Day 33 serum against I-MVA
Lane 4: Rabbit # 1, Day 70 serum against I-MVA
Lane 5: Commercial α-vaccinia Ab against I-MVA

FIGURE 10

Example of Western Blot Assays with Sheep Antibodies

Lane 1: MW Markers
Lane 2: Sheep # 1, Day 0 serum against I-MVA
Lane 3: Sheep # 1, Day 37 serum against I-MVA

Antibodies from Orally Vaccinated Animals Neutralize Virus

FIGURE 12

Example of Complex Cellular and Humoral Immune Responses

Elicited by Immune Cells Stimulated with MVA

The Manufacturing Approach:

Closed Systems from Virus Propagation to Packaging

FIGURE 15

The Manufacturing Approach: Closed Systems and FDA Approved Devices

Closed culture bags
to grow vaccine I-MVA

Process with scalable, disposable manufacturing
components already approved for clinical use

FIGURE 16

The Manufacturing Approach: FDA Approved cGMP Components, Connectors and Closed, Integrated Systems Example of a Closed Isolation System with Pumps, Connectors, etc.

An Example of a Sample Pak for Oral Delivery

ORAL VACCINIA FORMULATION

BACKGROUND AND SIGNIFICANCE OF THE INVENTION

Currently, international concern is heightened regarding the potential use of smallpox (variola) virus as a bioterrorism agent [1],[2]. This concern has increased since the tragic events around September 11$^{th}$ and the fall of 2001, particularly since the virus has been eradicated [3]. Thus, the recommendations developed by key advisory groups, such as the CDC Advisory Committee on Immunization Practices (ACIP) regarding vaccinia (smallpox) vaccine and the potential use of smallpox virus as a biological weapon (Modlin, 2001; see www.cdc.gov) are important guidance documents. Recommendations from the ACIP included the need to develop new vaccines, particularly a reformulated vaccine produced using cell culture techniques, and better research reagents and methods for therapy based on more modern technologies. Additional recommendations regarding vaccination of persons at various levels of risk, including acute or workplace exposure to infectious or highly attenuated strains, have been revised as part of those recommendations.

The degree to which the individuals who received the original smallpox vaccinations are protected is still a matter of conjecture and debate [3–7]. It is well known that long-lasting protective immune responses against vaccinia virus have been historically documented [3]. Cytotoxic T lymphocytes (CTLs; CD4+ and CD8+) are generated following immunization and memory T cells can be re-stimulated many years later by a variety of in vitro methods [6], and kinetics of antibody formation upon re-vaccination have been defined [8].

As reported by the ACIP and other sources (e.g., see www.cdc.gov), Dryvax,® the vaccinia (smallpox) vaccine currently licensed in the United States, is a lyophilized, live-virus preparation of infectious vaccinia virus (Wyeth Laboratories, Inc., Marietta, Pa.). The vaccinia vaccine does not contain smallpox (variola) virus. Previously, the vaccine had been prepared from calf lymph with a seed virus derived from the New York City Board of Health (NYCBOH, 9) strain of vaccinia virus and has a concentration of about $10^8$ pock-forming units (PFU)/ml. Vaccine was administered by using the multiple-puncture technique with a bifurcated needle. Although generally not life-threatening, there are some side effects in a subset of immunized individuals, particularly those who are immunosuppressed. Current stockpiles of vaccine kept at the CDC are inadequate, even when only high-risk for exposure individuals (e.g., military personnel and "first responders" ) are targeted for potential immunization with dilute vaccine, but particularly so in the case of a national emergency. Because the vaccine technology for vaccine production and immunization against smallpox is very old and stockpiles are inadequate in light of potential bioterrorism with smallpox, there is a need for better vaccines, state-of-the art methods of large-scale vaccine production and safer methods for re-immunization as well as de novo immunization of individuals at risk or for immunization of the public in the case of a national emergency. Furthermore, even though recent work indicates that diluted stockpiled vaccine is still immunogenic, even at dilute doses (39,40), the use of the NYCBOH strain and bifurcated needle delivery techniques are fraught with the problems of a replicating virus that can ooze from pustules at the immunization site consequently posing a potential threat to immunocompromised individuals.

Vaccinia virus strains with changed virulence have been developed and provide useful vectors for gene therapy and other applications [10]. The most attenuated strain, MVA, has acquired multiple deletions and mutations through serial passage [11–14]. The virus can replicate in chick embryo fibroblasts, but it has a very limited mammalian host cell range. Human cells are non-permissive for virus replication, which is blocked in the late stage of infection. The recommended mammalian host cell is the baby hamster kidney 21 clone 13 (BHK21-CL13) cell line [15].

Many studies support the selection of MVA as a therapeutic or prophylactic vaccine in humans. The virus has been used effectively for primary vaccination against smallpox in a test of 120,000 recipient vaccines [11]. When used as a vector, MVA has proved to be an efficient system because it expresses high levels of heterologous microbial and tumor antigen genes [13–21] in the absence of viral replication [18, 21]. An added margin of safety has been demonstrated from use of this strain in animals and human clinical studies [22–26], including immunocompromised individuals [27–33]. Of particular relevance to oral delivery are studies of Belyakov et al. [34] demonstrating strong mucosal and systemic immunity following intrarectal administration of recombinant MVA in a mouse vaccine therapy model.

In addition to safety and efficacy, oral immunization with replication-deficient recombinant vaccinia virus such as MVA, offers many other advantages over other vaccine candidates. The method effectively induces immune response in all three arms of the immune system, i.e., serum antibody, mucosal IgA antibody, and cell-mediated immunity. Compliance may be increased and overall costs reduced, because use of an oral rather than a parenteral vaccine may enhance patient (and/or parental) acceptance and would obviate the need for syringes and needles. Recombinant MVA can be constructed for multivalent vaccine or as a cocktail of MVA vaccines. Lyophilized vaccinia is extremely heat-stable. Heating to 100° C. for two hours led to a loss of only one log of infectivity, and storage at 45° C. for 2 years was still 100% successful in vaccination of volunteers [35]. These properties make oral MVA an ideal candidate vaccine.

Large-scale production of MVA is envisioned as a safe and immediate vaccination approach. Validation of vaccine safety and efficacy by bioassay on human intestinal cells is one method in the scope of evaluation of MVA safety so that it meets pre-clinical and clinical testing standards for vaccine production. The human intestinal cells are nonpermissive for the virus, as are other human cells, but they produce viral antigens that are recognized by the host's immune effector cells to stimulate systemic and mucosal immunity. A further benefit to the use of the intestine-derived cells as part of the testing and validation regimen is that it is well recognized that these types of epithelial cells can also act as antigen presenting cells in vivo. Thus, this is an excellent approach to induce effective immunity.

REFERENCES

The following is a listing of patents pertaining to smallpox vaccine, vaccinia vectors, recombinant vaccinia virus, genetic (i.e., DNA) vaccines, other poxviruses as vectors, or vaccine therapies.

| PATENT NO. | TITLE |
|---|---|
| 6,267,965 | Recombinant poxvirus-cytomegalovirus compositions and uses |
| 6,265,189 | Pox virus containing DNA encoding a cytokine and/or a tumor associated antigen |
| 6,265,183 | Direct molecular cloning of foreign genes into poxviruses and methods for the preparation of recombinant proteins |
| 6,165,460 | Generation of immune responses to prostate-specific antigen (PSA) |
| 6,103,244 | Methods for generating immune responses employing modified vaccinia of fowlpox viruses |
| 6,045,802 | Enhanced immune response to an antigen by a composition of a virus expressing the antigen with a recombinant virus expressing an immunostimulatory molecule |
| 5,997,878 | Recombinant poxvirus-cytomegalovirus, compositions and uses |
| 5,989,561 | Recombinant poxvirus-calicivirus rabbit hemorrhagic disease virus (RHDV) compositions and uses |
| 5,942,235 | Recombinant poxvirus compositions and methods of inducing immune responses |
| 5,863,542 | Recombinant attenuated AL V AC canaryopox virus containing heterologous HIV or SIV inserts |
| 5,858,373 | Recombinant poxvirus-feline infectious peritonitis virus, compositions thereof and methods for making and using them |
| 5,843,456 | Alvac poxvirus-rabies compositions and combination compositions and uses |
| 5,833,975 | Canarypox virus expressing cytokine and/or tumor-associated antigen DNA sequence |
| 5,766,599 | Trova fowl pox virus recombinants comprising heterologous inserts |
| 5,766,597 | Malaria recombinant poxviruses |
| 5,762,938 | Modified recombinant vaccinia virus and expression vectors thereof |
| 5,756,103 | Alvac canarypox virus recombinants comprising heterlogous inserts |
| 5,756,102 | Poxvirus-canine distemper virus (CDV) recombinants and compositions and methods employing the recombinants |
| 5,723,283 | Method and composition for an early vaccine to protect against both common infectious diseases and chronic immune mediated disorders or their sequelae |
| 5,691,449 | Respiratory syncytial virus vaccines |
| 5,688,920 | Nucleotide and amino acid sequences for canine herpesvirus GB, GC and GD and uses therefor |
| 5,494,807 | NYV AC vaccinia virus recombinants comprising heterologous inserts |
| 5,364,773 | Genetically engineered vaccine strain |
| 5,348,741 | Vector for recombinant poxvirus expressing rabies virus glycoprotein |
| 5,294,548 | Recombianant Hepatitis a virus |
| 5,266,313 | Raccoon poxvirus as a gene expression and vaccine vector for genes of rabies virus and other organisms |
| 5,262,177 | Recombinant viruses encoding the human melanoma-associated antigen |
| 5,223,254 | Respiratory syncytial virus: vaccines |
| 5,196,338 | Recombinant vectors for Haemophilus influenzae peptides and proteins |
| 5,171,665 | Monoclonal antibody to novel antigen associated with human tumors |
| 5,141,742 | Vaccines against melanoma |
| 5,134,075 | Monoclonal antibody to novel antigen associated with human tumors |
| 5,110,908 | Haemophilus influenzae peptides and proteins |
| 5,108,744 | Vaccines for Haemophilus influenzae |
| 5,098,997 | Vaccines for Haemophilus influenzae |
| 5,081,029 | Methods of adoptive immunotherapy for treatment of aids |
| 5,068,106 | t-PA solution of high concentration and use of the solution in human and veterinary medicine |
| 5,021,347 | Recombinant vaccinia virus expressing E-protein of Japanese encephalitis virus |
| 4,920,213 | Method and compositions useful in preventing equine influenza |
| 4,877,612 | Immunological adjuvant and process for preparing the same, pharmaceutical compositions, and process |
| 4,738,846 | Vaccine for vesicular stomatitis virus |
| 4,631,191 | Methods and compositions useful in preventing equine influenza |
| 4,603,122 | Antiviral agent against herpes virus infections |
| 4,567,147 | Attenuated smallpox vaccine strain |
| 4,315,914 | Pharmaceutical compositions useful as cellular immunopotentiator and antitumor agent and process for production thereof |
| 4,315,001 | 2-Deoxy glucose as an antiviral agent against herpes simplex |
| 4,301,150 | Method of treating the clinical manifestations of viral diseases |
| 4,218,436 | Compounds and methods |
| 4,192,799 | Conjugates formed by reacting a prostaglandin mimic compound with a carrier molecule |
| 4,049,798 | Method for the treatment of Herpes Simplex |

In addition to the patents listed in this section, non-patent publications cited in this application can be found in Section VI. (D) "Literature Cited" below.

SUMMARY OF THE INVENTION

The oral vaccine system and methods described herein use a live, defective vaccinia virus or a viral antigen preparation of such a virus, that can confer anti-smallpox immunity in the recipient. The invention encompasses the combined methods by which the virus is grown using in vitro cell culture methods (e.g., the methods of growing the I-MVA in the baby hamster kidney cell line, BHK-21, followed by steps to purify the virus, and quantitate the dosage), the characterization bioassays for its safety and efficacy prior to clinical use by oral delivery as per the immunization protocol, and the methods and components used for formulation. Cells used for vaccine preparation are derived from INCELL's reference Master Cell Bank (MCB) and Working Cell Bank (WCB: n>200 vials) stocks. The MVA virus is propagated, for example, on BHK-21 cells that are cultured to high culture density on microcarrier beads in plastic cell culture bags.

The vaccinia virus used for the vaccine can derive from the I-MVA strain or other defective vaccinia virus (DVV) strain incapable of generating infectious virus in a complete lytic cycle in human cells, but able to replicate in an animal host cell which is permissive for the virus.

Safety, efficacy and potency components of the invention include in vitro and immunoassays to evaluate the potential safety and potency using surrogate endpoint assays, such as infection of human intestinal cells, or other defined alimentary tract epithelial cells, and cell mediated immune (CMI) responses of cells from anti-vaccinia immunized individuals. The CMI responses can include bioassays for cytokines, cytotoxicity or other in vitro methods that reflect what would occur in vivo.

The vaccine might be packaged in various forms, including packaging in a liquid, gel, or solid form that may be a tablet or gelcap or a component of a food carrier material, such as a pudding or yogurt. In particular the live vaccine would require packaging in a form that would allow delivery into the human alimentary tract as whole virions that could be taken up in at the first part of the alimentary tract, i.e., the oral cavity, or at other sites, such as the intestine.

Various embodiments of the invention disclosed herein employ vaccinia virus, which was developed for gene therapy applications and has been used as a vector to deliver genes, (e.g., tumor or microbial antigen genes), to the host as a live vaccine and carrying information intended to confer immunity on the host by expression of the delivered gene.

The principle use of the oral vaccine system will be to protect against potential poxvirus infection, including smallpox, but incorporation of other genes into the vaccinia virus vector is envisaged, such that multi-valent vaccine(s) against a variety of potential bio-agents, potential pathogens, or products of pathogens (e.g., toxins) can be prepared for oral delivery as disclosed herein. These can be packaged as separate packages or may be in the same vector. They may be in a single package or multiple packages, as another use of the invention.

BRIEF DESCRIPTION OF THE DRAWINGS

FIG. 1. BHK-21 Cells Growing in Culture. This figure shows the morphology of normal BHK-21 clone 13 cells growing in monolayers. The cells were fixed with Omnifix and stained with Giemsa.

FIG. 2. Immunoplaque Focus Formation Assay in BHK Cells to Titer Virus. This FIG. shows BHK cells with stained, I-MVA infected foci (arrows). Some stained individual cells are also seen, but they are not counted in this assay.

FIG. 3. Serum Anti-MVA Antibody Titre in Rabbit Immunized by Intramuscular Route Measured by ELISA Assay. The rabbit was immunized with I-MVA in PBS combined with TiterMax Gold. ELISA was performed on MVA-coated microtiter plates and read at 405 nm after detection with PNPP colorimetric assay.

FIG. 4. Serum Anti-MVA Antibody Titre in Rabbit Immunized by the Intramuscular Route Measured by ELISA Assay. The rabbit was immunized and the ELISA was performed as described above in FIG. 3.

FIG. 5. Serum Anti-MVA Antibody Titre in Sheep Immunized by the Intramuscular Route Measured by ELISA Assay. The sheep was immunized with I-MVA in PBS combined with TitreMax Gold. The ELISA was performed as described above in FIG. 3.

FIG. 6. ELISA Assays of Orally Immunized Rabbit Antibodies at Early Immunization Time Compared to Pre-bleed. The rabbit was immunized with I-MVA formulated for oral delivery. ELISA assays were performed as described above in FIG. 3. The orally immunized rabbit produces detectable anti-MVA antibodies by day 19 compared to the pre-bleed.

FIG. 7. ELISA Assays of Orally Immunized Rabbit Antibodies Show Continued Antibody Production. An orally immunized rabbit continues to produce anti-MVA antibodies, with slightly declining titers on day 69 compared to day 46. ELISA was performed as described above in FIG. 3.

FIG. 8. ELISA Assays of Orally Immunized Sheep Antibodies. The sheen was immunized with I-MVA formulated for oral delivery. ELISA assays were performed as described above in FIG. 3.

FIG. 9. Comparative ELISA Assay of INCELL Antibody vs. Commercial Antibody. INCELL rabbit anti-MVA antibodies are equal to or better than commercial antibodies and have a very high titer in serum and as purified IgG when tested for binding to purified I-MVA in ELISA assays. ELISA assays were performed as described above in FIG. 3.

FIG. 10. Western Blot Assays with Rabbit Antibodies. Antibodies from immunized rabbits recognized purified I-MVA proteins. Purified I-MVA was run on gels, and separate lanes were tested for recognition of viral bands by the test antibodies indicated.

FIG. 11. Western Blot Assays with Sheep Antibodies. Purified MVA was run on gels and separate lanes were tested for recognition of viral bands by the test antibodies indicated.

FIG. 12. Antibodies from Orally Vaccinated Animals Neutralize Virus. Sera from test animals used in immunoplaque assays showed infectious I-MVA neutralization as measured by inhibition of plaque formation compared to the controls (100%). Serum dilution is shown on the x-axis. Test animals: R3-37: Orally Immunized Rabbit 3 (day 37 pi): R4-37: Orally Immunized Rabbit 4 (day 37 pi): S2-19: Orally Immunized Shee 2 (day 19 pi).

FIG. 13. MVA-Stimulation of DNA Synthesis in PBMCs. This figure shows demonstrable stimulation of DNA synthesis in PBMCs from a sheen immunized i.m. ("S-1") and a sheep immunized orally ("S-2").

FIG. 14. Complex Cellular and Humoral Immune Responses Elicited from Immune Cells Stimulated with MVA. This is a diagram representing the complex humoral and cell-mediated immune responses, and examples of test parameters to assess immune responses against MVA, using in vitro surrogate models to evaluate safety, efficacy and potency of the orally delivered vaccine. The example is also applicable to other DVV and other target cells, effector cells, and infected cells. Similarly, the test methods would be applicable to other orally delivered virus stocks intended to be ingested as a means of delivery of the vaccine. PBMCs: Peripheral blood mononuclear cells: SI: small intestine cells.

FIG. 15. The Manufacturing Approach: Closed Systems from Virus Propagation to Packaging. This is a diagram representing a systematic way to develop and manufacture vaccine product in a closed system using available devices and clinical tools.

FIG. 16. The Manufacturing Approach: Closed and FDA Approved Devices. This is a diagram representing some examples of the types of devices useful for small-scale manufacturing. There are many other similar devices and larger scale options.

Figure 17:
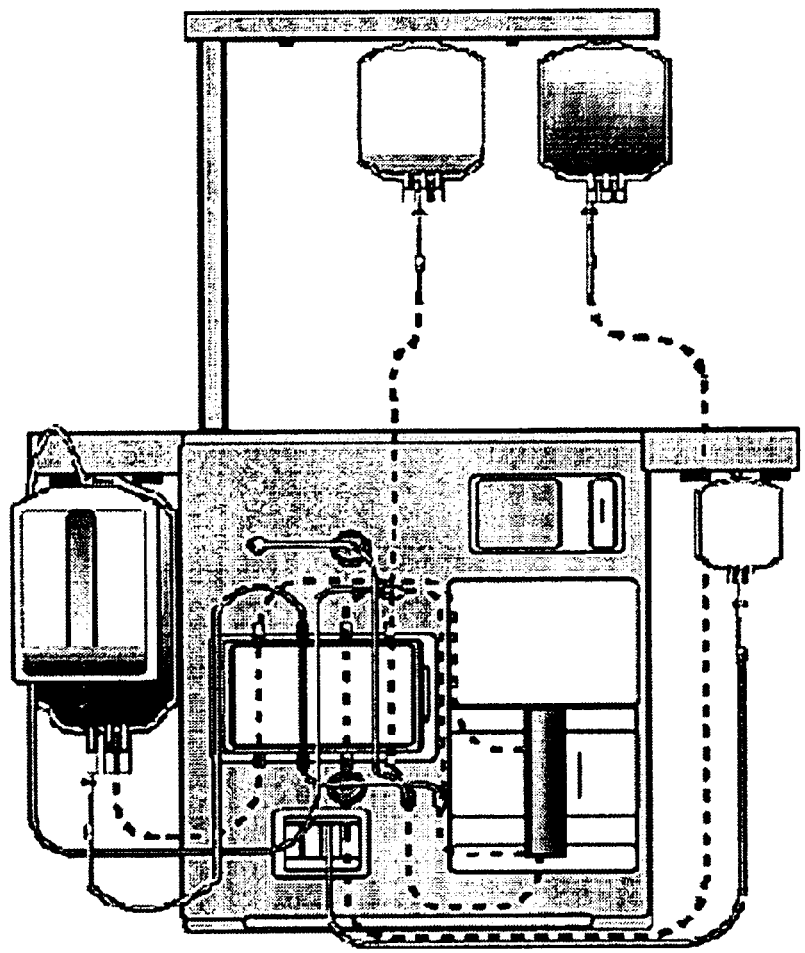

FIG. 17. The Manufacturing Approach: FDA Approved cGMP Components, Connectors, and Closed, Integrated Systems. Example of a closed isolation system with pumps, connectors, etc. that would comprise integrated components that are easily configured and disposable.

Figure 18:

FIG. 18. An Example of a Sample Pak for Oral Delivery. This is a representative sample of the types of packaging that might be used for unit dose delivery of the vaccine product as a tablet, a paste, or a gel. There are many types of packaging and options such as blister packing that might be the preferred method.

DETAILED DESCRIPTION OF THE INVENTION

A. Manufacturing Methods and Materials

1. Facilities and Standards

All cells, virus and reagents are handled according to cGMP (current Good Manufacturing Practice) standards. The manufacturing facility (anteroom, class 10,000 room, class 100 hoods) staff will use SOPs that meet FDA testing, validation, and QA/QC manufacturing standards. These measures are taken to accelerate the process from discovery to product.

2. The BHK-21 Clone 13 (BHK21-CL13} Cell Line

The BHK-21 CL 13 cell line (ATCC #CCL-10) is used as the permissive cells to propagate the stock virus. The rationale for choosing this line is that it is permissive for DVV such as MVA and is easily grown in culture. An example showing BHK-21 cells growing in culture is shown in FIG. 1. Cells are maintained as recommended by the ATCC in a modified Minimal Essential Medium with Earle's Salts [EMEM], 0.1 mM non-essential amino acids, and 1 mM sodium pyruvate (e.g., GIBCO or other vendor) with 10% v/v fetal bovine serum (FBS; e.g., Hyclone or other vendor), or another suitable growth medium. They are subcultured using 0.25% trypsin, 0.03% EDTA (GIBCO) at subcultivation ratios of 1:2 to 1:10. Cells used for vaccine preparation are derived from INCELL's reference Master Cell Bank (MCB) and Working Cell Bank (WCB; n≧200 vials) stocks. The banked cells have been checked for sterility by standard microbial growth and mycoplasma PCR assays of the MCB and WCB and characterized by DNA fingerprinting to assure identity.

3. Virus Propagation and Analyses

The INCELL propagated strain of MVA (ATCC #VR01508), designated I-MVA, has been routinely propagated by standard methods and titered by the preferred method of immunoplaque assay as detailed below. Other quantitative methods that have been used include either end point dilution in BHK-21 cells to obtain a 50% tissue culture infectious dose (TCID50/ml) or IU (infectious units), as detailed by Dresden et al. [15]. For in vitro and in vivo assays, virus has been purified by ultracentrifugation through a 36% sucrose cushion using standard virus purification methods. The BHK-21 cells are grown in culture (also termed "in vitro") and infected at 0.1 FFU per cell to generate large lots of virus harvested at 72+/−2 hours post infection (p.i). The BHK-21 cell cultures can be monolayers in various types of bioreactor or scale-up cultures, including culture flasks, stacked systems, culture microcarrier beads, or other appropriate substrates to culture the cells. The resultant virus stocks can be concentrated or purified by ultracentrifugation, ultrafiltration, or other standard methods, then titered on BHK-21 cells and stored for packaging. Part of the stock is aliquoted for use in the bioassays and for QA testing. All lot information is entered into the master database and inventory management system which were developed as part of the invention and its use.

Figure 2:
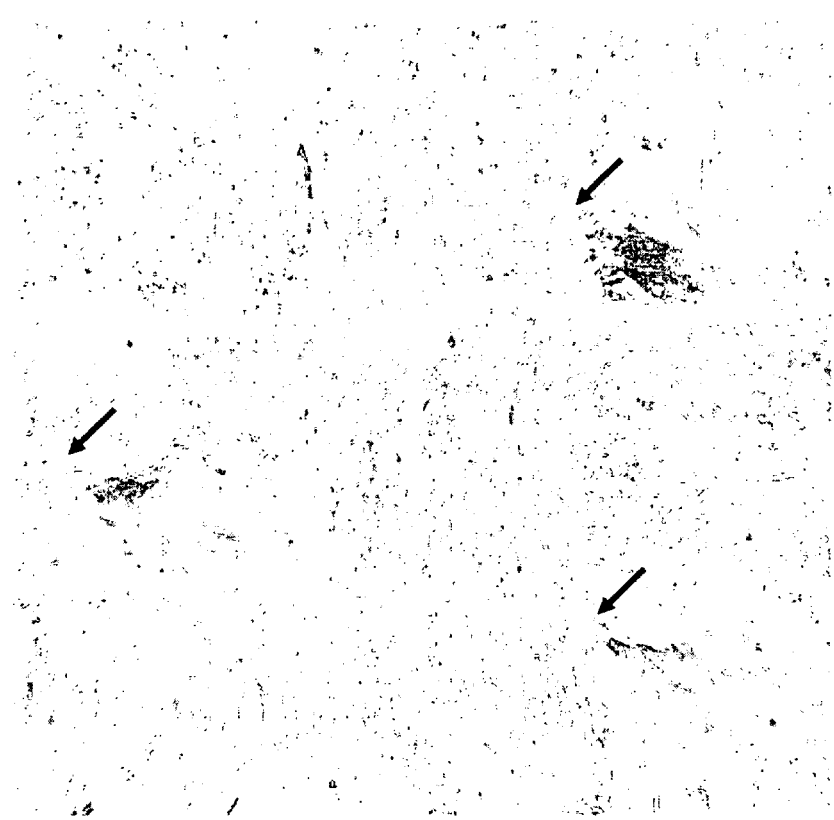
Figure 3:
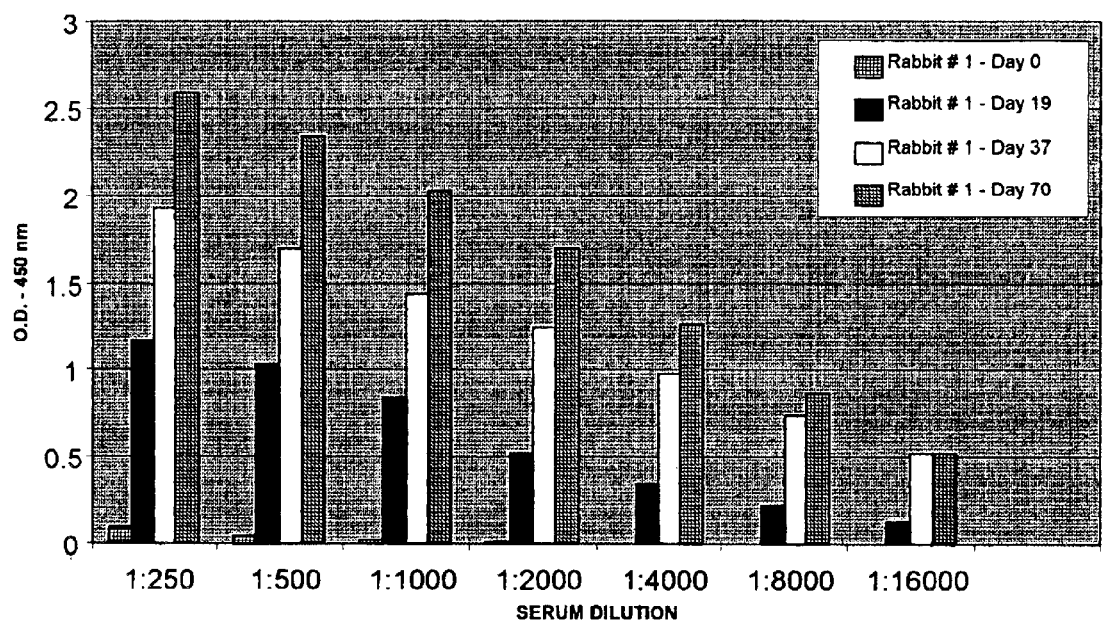
Figure 4:
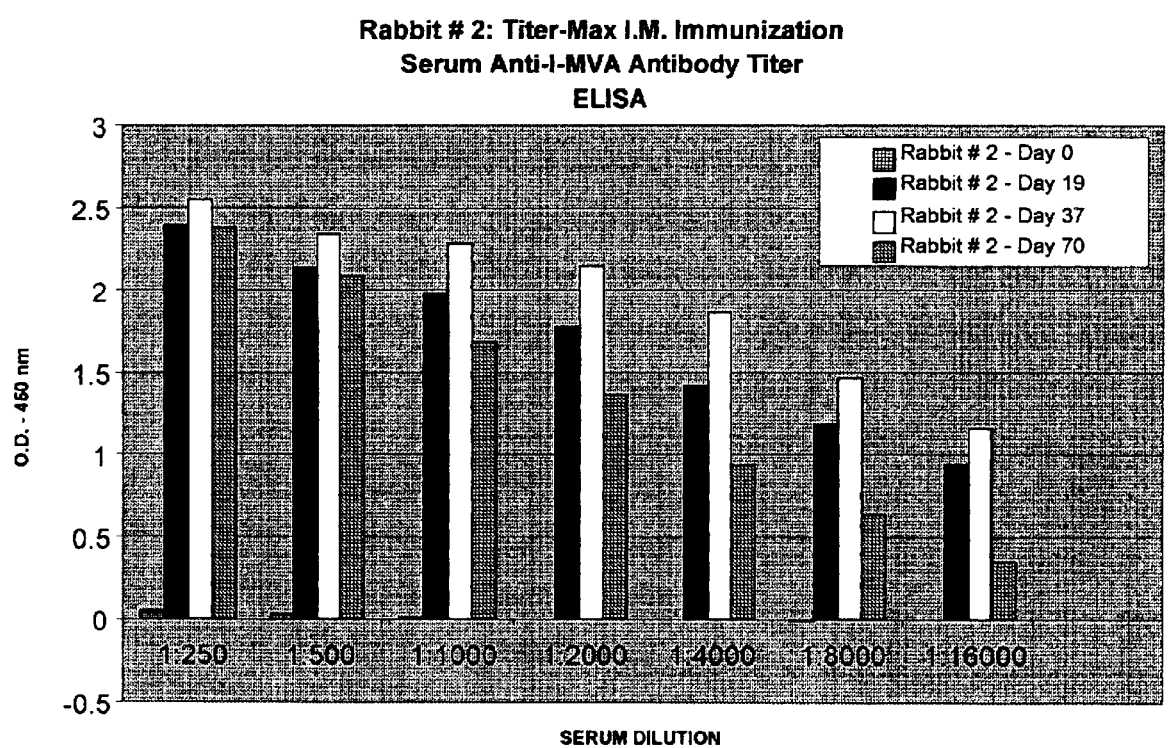
Figure 5:
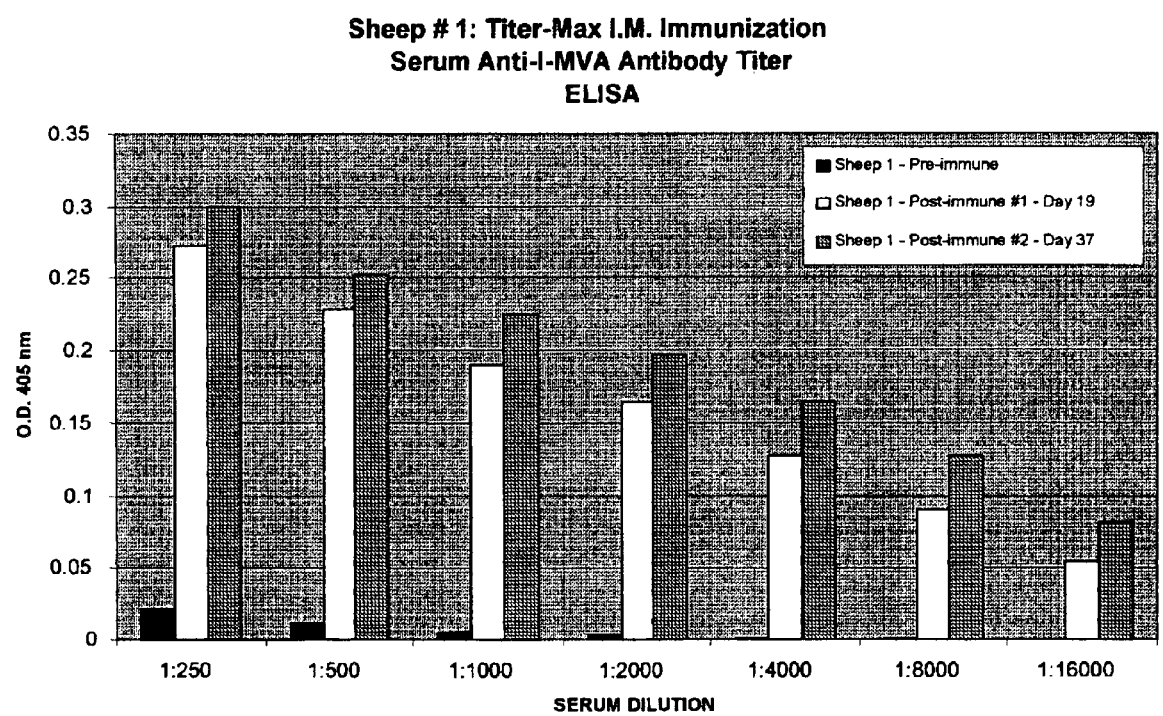
Figure 6:
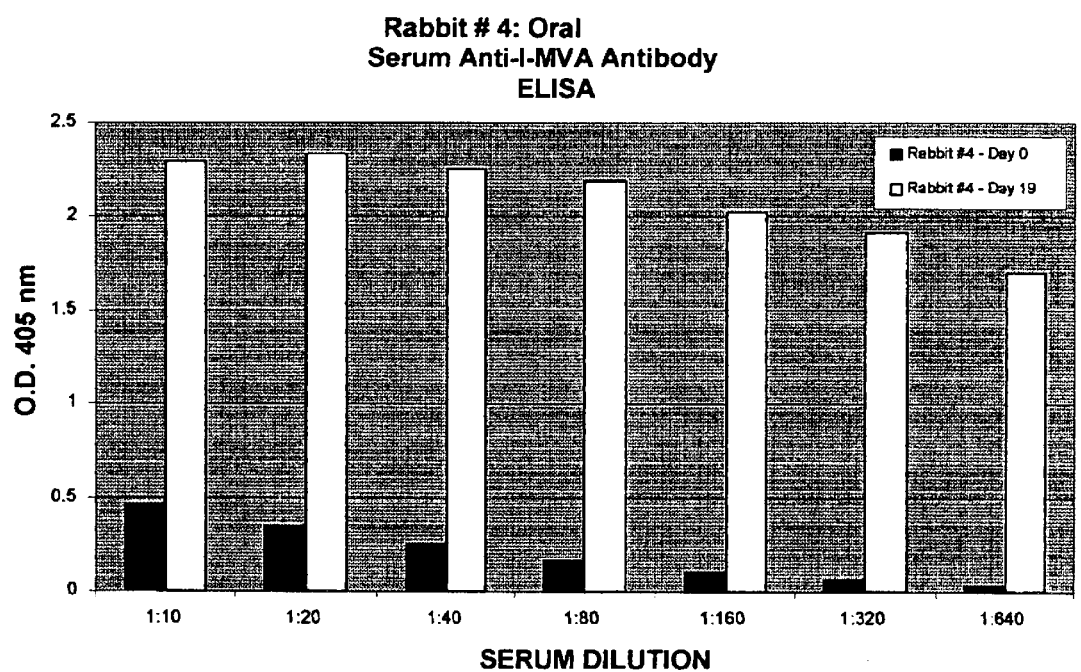
Figure 7:
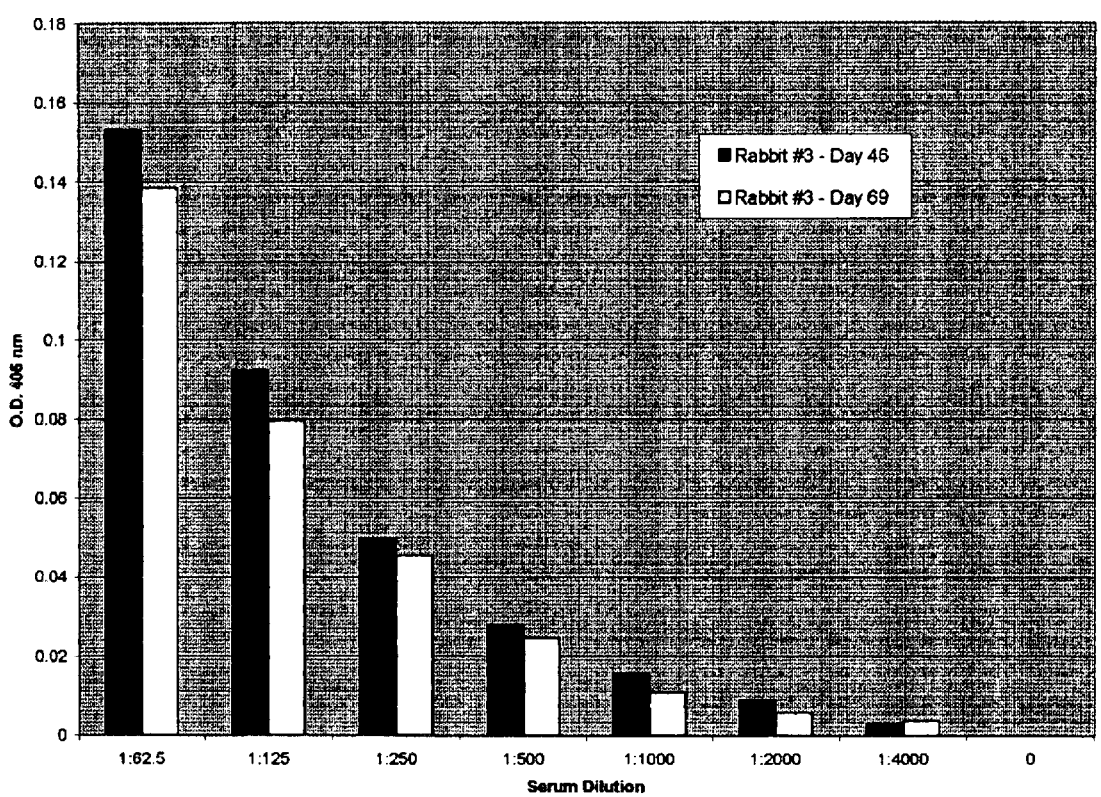
Figure 9:
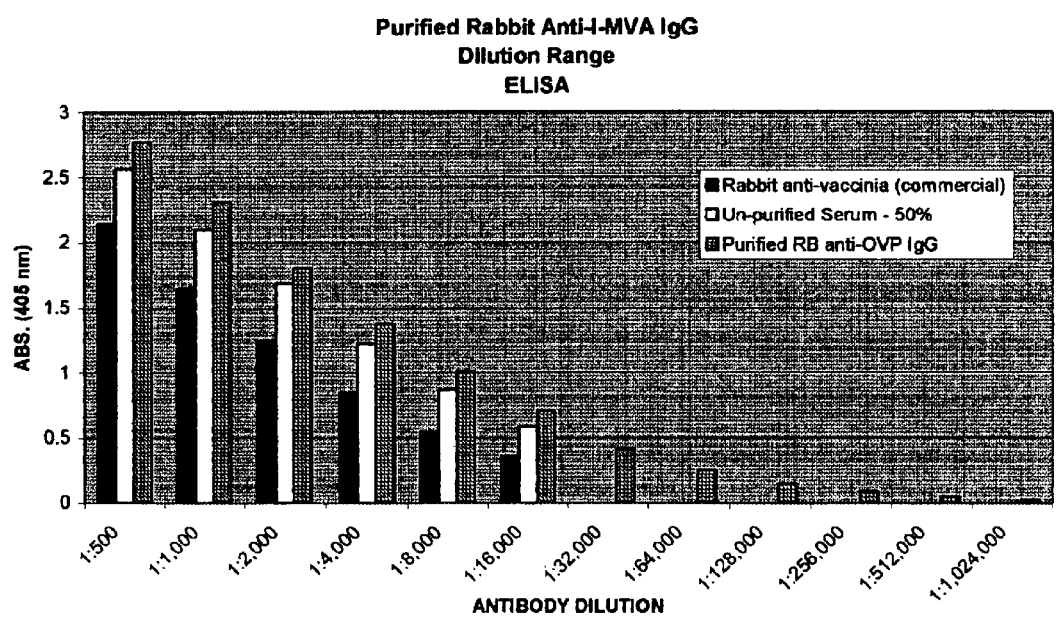

For immunoplaque assays, BHK-21 cells are seeded at a density of $4.5 \times 10^4$ cells per well of a 24-well plate in growth medium (EMEM, 10% FBS, plus additives, as described above). After overnight attachment, when the cells are 80–90% confluent, they are infected with I-MVA by mixing the virus with EMEM prepared as per the growth medium but with 2% rather than 10% FBS (=EMEM:2 infectivity medium). Test I-MVA source materials are generally diluted in $10^{-3}$ to $10^{-7}$ for cell culture derived, unconcentrated supernatants, and $10^{-6}$ to $10^{-10}$ for gradient centrifugation purified or otherwise concentrated (e.g., ultrafiltered) virus. Dilutions are made in EMEM:2 infectivity medium. Cells that receive no virus but are otherwise incubated with EMEM:2 infectivity medium and treated the same are used as negative controls. Reference virus stocks that are known to produce 100-200 plaques per well are included in the assays as positive controls to assure performance of the assay. Cultures are gently swirled to assure even virus distribution then incubated for 24 hr at 37° C., in a 5% $CO_2$, 95% air environment. At the end of the incubation period, the medium is removed from the wells, the cells are fixed with 0.5 ml 1:1 acetone:methanol for 5 min, the fixative is removed and 1 ml CMF-PBS is added to each well. The rinse solution is removed and anti-vaccinia virus primary antibodies (e.g., rabbit, sheep, human or other source) and the biotin or other chromagen-labeled secondary antibodies used at an effective dilution (e.g., 1:500 to 1:1000) to easily visualize the immunoplaques. For most studies, 1:500 dilutions of each of the primary (rabbit anti-vaccinia; Accurate Chemical or INCELL-prepared) and secondary (HRP anti-rabbit IgG; SIGMA or other vendor) antibodies were used. An example showing BHK-21 cells and the appearance of plaques in the immunoplaque assay is shown in FIG. 2.

B. Antiviral Antibodies and Applications

1. Intramuscular Depot Immunization with TiterMax Gold

For rabbit immunizations, $10^8$ FFU in 0.5 ml PBS were combined with 0.5 ml TiterMax Gold using a double hub emulsification needle (push antigen into TiterMax first, aqueous into oil phase) for mixing. The emulsion was injected into 4 sites (0.2 ml each) over both shoulders and both hind quadriceps. For sheep immunizations, $2 \times 10^8$ FFU in 1 ml PBS were combined with 1 ml TiterMax Gold as above and inject 0.4 ml twice into each hind quadriceps. Animals were bled periodically to test antibody production. Good antibody titers are present within 4–6 weeks and remain high for several months.

2. Oral Immunization Formulae and Methods

A variety of oral immunization formulae can be used for immunization. Oral immunization is done by preparing a formula in which the virus remains viable (as determined by infectivity of released virus from the orally delivered paste and separate components of the paste formulae listed below) and is captured in nanoparticles and micelles as part of the protective formulation that includes aqueous and oil-based components, as well as suspending agents and carriers that protect the virus from degradation and allow it to be absorbed from the oral cavity and the intestine.

As an example of the formulation used for the the studies shown in the Figures, virus is prepared ( $2 \times 10^8$ per sheep) by mixing virus in a solution of Hetastarch (hydroxyethyl starch, clinical grade; 6% w/v; Baxter), 40% (v/v) mannitol [UPS grade higher; SIGMA or other vendor], 0.15% (v/v) AAFA™ (nutritional supplement grade fish oil; INCELL 5% (v/v) glycerol (UPS grade; SIGMA or other vendor), 0.5% (w/v) gelatin (SIGMA) at a volume that will achieve a final concentration of $5 \times 10^4$ to $2 \times 10^8$ infectious FFU, depending on the effective or test dose expected (e.g., $10^6$ to $10^8$ for humans, depending on immunization status). In the animal studies, doses were at $10^8$ per rabbit and $2 \times 10^8$ per sheep. Gel-sol virus carrier (GSVC) excipient components were prepared as an equal mixture (1:1:1; Avicel® CE-15(microcrystalline cellulose and guar gum), Avicel® 591 (water-dispersible microcrystalline cellulose containing sodium carboxymethylcellulose (NaCMC) and Ac-Di-Sol® (internally-crosslinked, water insoluble sodium carboxymethylcellulose (NaCMC)) [source of all components: FMC Products]) which was slowly added (with vortexing) to a final concentration of 10% (w/v).

Taste-testing (humans and animals) revealed that the formulae was palatable as a slightly sweet paste-gel type of formulae that caused no aftertaste and which could be subsequently dried (e.g., for tableting) and still maintain infectious virus as measured by infection of dissolved materials on BHK-21 cells after they had been dried and stored for various time periods, supporting long-term storage as a tablet or paste-gel material that maintains biological activity.

C. Bioassays and Biochemical Methods for Safety, Efficacy and Potency

A variety of bioassays and biochemical analyses are done to evaluate the vaccine. These include: (a) human cell line nonpermissiveness with expression of vaccine antigens (a safety test); (b) viral antigen expression and production compared to previous lots and reference standards (i.e., potency); and (c) activation of humoral and cell-mediated immunity (e.g., potency and efficacy) in infected animals. These are imperative types of assays to evaluate each virus lot and the overall potential variability between lots of virus.

1. Safety and Potency Bioassays: I-MVA Infection of Human Cells in vitro

INCELL has the only long-term continuous cell lines derived from human intestine (HI). As part of the pre-clinical testing, the HI cells were be grown in M3:10™ medium (INCELL) as monolayer cultures using standard methods so that they maintained functional cell and organ-specific markers that make them useful in vitro surrogates for orally administered products, including vaccines or drugs. Master and Working Cell Banks of these cells were banked in the INCELL repository prior to initiating these studies.

As part of the evaluation of I-MVA lots of oral vaccine, the HI test cell line(s) lines were seeded into culture vessels in M3:10™ (INCELL) growth medium, allowed to attach, then infected with test lots of virus essentially as described above for the FFU immunoplaque assays or as detailed elsewhere (15) for alternate cell infectivity studies. For each set, parallel cultures of uninfected and infected permissive BHK-21 cell controls, and dilutions of prepared reference virus, were tested to validate the bioactivity of the virus stocks.

An example of the study showing comparative infectivity of I-MVA for human intestinal and other human cells compared to the permissive BHK-21 cells are shown in Table 1. The important vaccine safety-related conclusion from the results shown in this table is that the I-MVA strain used to prepare the vaccine does not grow in human cells but readily replicates in the permissive BHK-21 cells.

TABLE 1

Safety Assays: I-MVA Does Not Replicate in Human Cells

| Description of Test Groups* | Cell Line Designation | 48 hr p.i. Virus Titer** |
|---|---|---|
| Starting Inoculum | NA: virus only | $1 \times 10^5$ |
| Positive Control | BHK-21 | $1.3 \times 10^7$ |
| Negative Control | NA: media + virus only | $4.3 \times 10^4$ |

| Description of Human Cells Tested | Cell Line Designation | 48 hr p.i. Virus Titer |
|---|---|---|
| Normal Duodenum | HUD 00818 | $<10^5$ |
| Normal Duodenum | HUD 00919 | $<10^5$ |
| Normal Jejunum | INJE 00510a | $<10^5$ |
| Normal Jejunum | INJE 00526a | $<10^5$ |
| Normal Jejunum | INJE 00729 | $<10^5$ |
| Normal Ileum | INIL 00510a | $<10^5$ |
| Normal Ileum | INIL 00729 | $<10^5$ |
| Normal Colon | NCM 356 | $<10^5$ |
| Normal Colon | NCM 425 | $<10^5$ |
| Normal Colon | NCM 460 | $<10^5$ |
| Normal Colon | CSC-1 | $<10^5$ |
| Colon Cancer | CaCo2 | $<10^5$ |
| Colon Cancer | Colo 205 | $<10^5$ |
| Normal Dermis | HSK 740DF | $<10^5$ |

*Cells seeded as monolayers, Infected with virus (MOIca. 0.1) At 48 hrs p.i., immunoplaque assays were done to determine titer.
**Titer shown refers to the FFU/ml of each cell line.
Note that the virus replicated in the permissive BHK cells but not in any of the human cell lines.

2. Immunoassays to Evaluate Antibodies and Antigens

Three methods are used to evaluate production of the viral antigens and anti-viral antibodies as a measure of potency of the lots produced: (a) ELISA assays, (b) Western blots, and (c) Immunocytology.

a. ELISA Assays

ELISA plate assays are done to quantitate the amount of anti-virus antibodies produced against the virus or the amount of virus antigen produced by infected cells. Such assays have many variables and methodologies. An example test method is as follows. The virus stocks are diluted to 0.1 to 4 µg/ml in carbonate buffer and coated onto ELISA 96-well plates at 25 µl/well for 4 hours to overnight at 37° C. and then washed 3 times with PBS-Tween40 (PBS-T). The antigen-coated plates are blocked with 3% BSA at 200 µl/ml for 1 hr at 37° C. (on a rocker platform) and washed 3 times with PBS-T. Virus reference test antigens and reference antibody dilutions are used at known positive concentrations and ratios as positive controls. Test antibodies are bracketed for assay at multiple dilutions, based on expected ranges, in replicates of N=4, with test dilution samples added to the plates at 25 µl/well. After incubation for 2 hr at 37° C., the plates are washed with PBS-T. All comparative values are analyzed using INCELL's customized plate analysis software in concert with statistical and graphics programs.

Importantly, antibodies have been consistently demonstrable in all of the immunized animals. In general the orally immunized animals had a somewhat lower titer than the animals that received intramuscular depot immunization with the TiterMax. However, as shown below, the circulating antibody titer did not necessarily correlate with neutralization differences and CMI may actually be higher in the orally immunized animals.

b. Western Blots

For Western blot analyses, cell protein lysates were prepared and resolved by electrophoresis on a SDS-8% polyacrylamide gel, then transferred onto nitrocellulose for 2 h in a buffer containing 25 mM Tris, 192 mM glycine, and 20% methanol (pH 8.6). The blots were blocked overnight at 4° C. in a PBS blocking buffer containing 1% BSA and 0.1% NP40 and then incubated for 1 h at room temperature with rabbit or sheep anti-vaccinia antibody diluted 100-fold in blocking buffer. After being washed with 0.1% NP40 in PBS, the blots were incubated for 1 h at room temperature with goat anti-rabbit or anti-sheep IgG light (Amersham) diluted 1000-fold in blocking buffer, washed again, and exposed to X-ray film for comparative evaluation and image analysis to quantify the samples.

Figure 11:
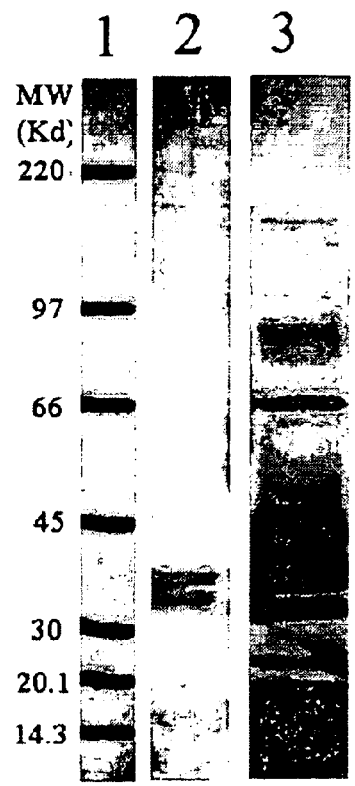

As shown in the examples of Western blots in FIGS. 10 and 11, the immunized rabbits and sheep were able to elicit antibodies that could recognize viral proteins on a Western blot analysis. This further verifies the specificity of the antibodies for the virus, as was demonstrated with sera from all of the test animals.

c. Immunocytology to Visualize for Antigen Expression by Infected Cells

Immunocytology assays may have many variables and methodologies. An example test method is as follows. To analyze cells for visualizing the expression of viral or cell antigens, the cells are grown as monolayers. This is done on multi-well plates or on Lab-Tek (Corning) slides or attached to coated slides by standard cytocentrifugation protocols. For immunodetection assays, standard protocols have primary antibody diluted in PBS to an optimal working dilution followed by incubation with the cells that have been fixed in Omnifix or another antigen appropriate fixative.

For immunocytology assays, the cells are fixed with 10% formalin (Sigma) for 1 hr at 4° C. and blocked with 3% bovine serum albumin (BSA; Sigma) in calcium- and magnesium-free phosphate buffered saline with 0.01% Tween-20 (CMF-PBS-T). Specific anti-vaccinia polyclonal rabbit antibody (Accurate Chemical) or newly derived antibodies are added to the fixed and rinsed cells. Cells are stained according to the general procedures detailed in the Vectastain® Elite ABC Kit by the manufacturer (Vector Laboratories). Briefly, each sample is incubated with test antibody at the appropriate working dilution of the antibody followed by a biotinylated goat anti-rabbit or anti-mouse secondary antibody (Sigma: 1:2000). The samples are quenched with 0.3% hydrogen peroxide and developed with a combination of an avidin-linked peroxidase conjugate and the 3,3'-diaminobenzidine (DAB) chromagen. The slides are counterstained with hematoxylin (Biomeda Corp.), mounted with aqueous mounting medium (Biomeda Corp), and visualized with a Nikon Microscope. Photographs are taken using a digitized format and photo capture software. The stained cells look similar to the individual stained cells shown in FIG. 2 of the immunoplaque assay. When such assays are done using antibodies from i.m. or orally immunized animals, the immunostained cells look similar.

3. Demonstration of Neutralizing Antibody and Protection in Immunized Animals

For immunoplaque reduction or neutralization assays, the methods are the same for immunoplaque assays through the set-up step, but the virus inoculum is pre-incubated for at least 1 hr with serum or purified IgG prior to adding the virus-antibody inoculum. Otherwise, the remaining steps of the protocol are they same. When the virus is pre-incubated with the test serum containing antibody the incubation step is at 37 C and the serum is usually heat-inactivated at 56 C for 30 min prior to incubation with the virus.

FIG. 12 shows that orally immunized animals could neutralize infectious I-MVA as measured by inhibition of plaque formation compared to the controls (100%). Similar results were obtained with i.m. immunized animals. It was concluded that all orally immunized animals produced neutralizing antibody. In the example, rabbits showed a stronger effect but sera were collected 37 days pi vs. only 19 days pi for the sheep.

This work complements studies done with mice in which orally immunized mice are challenged with an infectious vaccinia strain, such as WR, and the immunized animals are protected from the associate morbidity and mortality of the challenge virus.

4. Assessing Potency with Cell-Mediated Immunity Assays a. Cells from Immunized Donors The Peripheral Blood Mononuclear Cells (PBMCs) are obtained from peripheral blood and separated using standard methods. Either fresh PBMCs or pre-qualified (known responder) PBMCs from cryopreservation are used for testing. Cell separation methods and cell-mediated immunity assays may have many variables and methodologies as described below.

Figure 13:
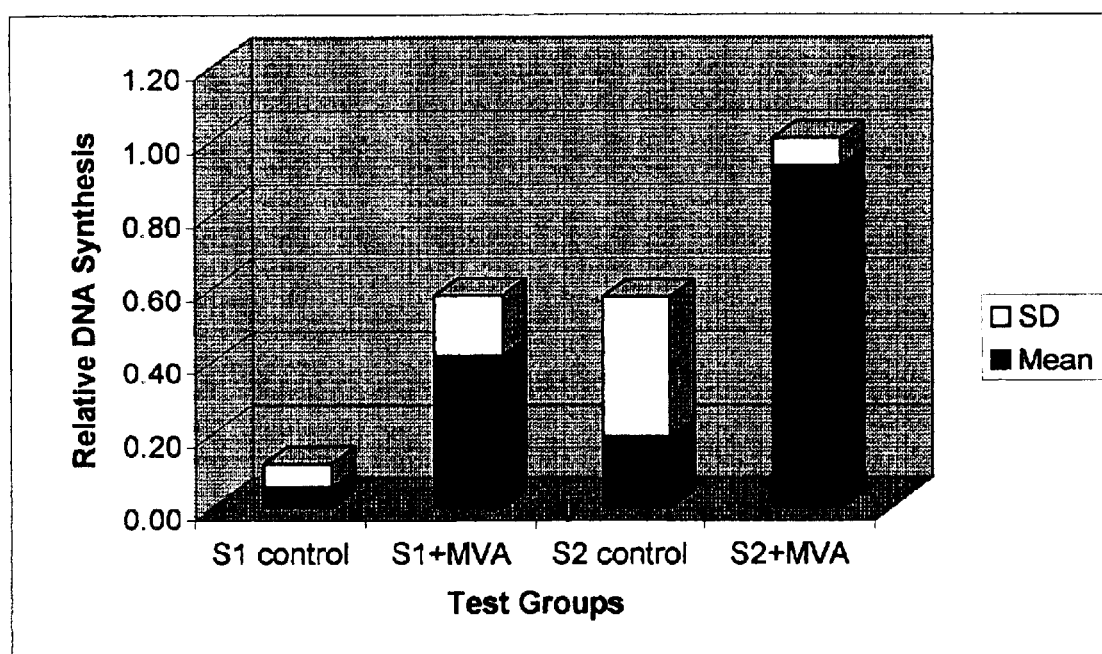
Figure 14:
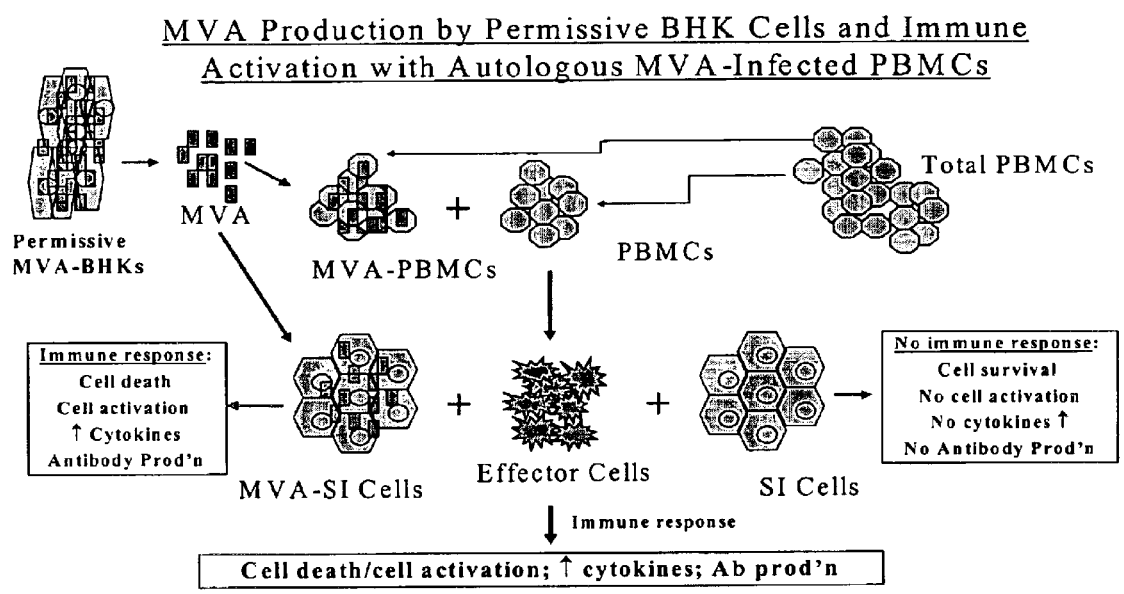

One example method is to take PBMCs from immunized donors and determine whether or not they can respond to stimulation with the immunizing antigen, in this case, I-MVA. To that end, PBMCs from a sheep immunized intramuscularly (i.e., "Sheep 1") and a sheep immunized orally (i.e., "Sheep 2") were added to RPMI culture medium containing 10% (v/v) autologous plasma. Quadruplicate cultures of $10^5$ cells per well of a 96-well plate with or without MVA antigen, or control wells without cells, were compared to assess a cellular response to MVA antigen as measured by stimulation of DNA synthesis using a BRDU ELISA-based assay as detailed below. Results of an example study are shown in FIG. 13, where it is clear that both sheep had demonstrable cell stimulation. The conclusion form these studies is that oral immunization can effectively induce cell-mediated immunity against I-MVA and,thus, presumably against a related invading poxvirus, such as smallpox.

Another example method is as follows. The collected blood cells or cultured cells are layered over warm Histopaque and centrifuged at 400×g to separate dead from viable cells. The number and viability of the cell population is assayed by standard 0.25% Trypan Blue Dye Exclusion using INCELL's SOP. On day zero, $5\times10^6$ viable cells are seeded into 6-well plates containing a final volume of 5 ml MR:20™ (INCELL) or other suitable culture medium. After an overnight culture adaptation period, a subset of PBMCs are infected with I-MVA at an MOI of 1 TCID/cell for 2 h and the remaining autologus PBMCs are readied for co-culture as described below. After washing twice, $8\times10^5$ I-MVA-infected PBMCs are irradiated or treated with mitomycin C (25 mcg/ml) so they can no longer divide. For CMI activation studies, the infected cells are then added to $5\times10^6$ autologous PBMCs, which had also been cultured overnight. After subsequent culture for 4–7 days, DNA synthesis is determined by adding radiolabeled $^3$H-thymidine or 5-Bromo-2-deoxyuridine (BRDU) for the final 4 to 18 hr of culture period to measure incorporation into DNA. The $^3$H-thymidine is measured by liquid scintillation counting of trichloroacetic acid [TCA] (10%)-precipitated cellular DNA added to scintillation fluid and counted. The BRDU is measured using an ELISA assay and highly specific anti-BRDU antibody linked to a chromagen (e.g., biotin). Control cultures (cells and media only) are grown at the same time but do not receive I-MVA or I-MVA infected cells. The control values are either subtracted from the test assays with infected cells to give specific incorporation numbers or they are used to determine the relative labeling index by the equation (DNA[t]-DNA[c])/DNA[c]).

To amplify the response or to initiate a de novo response, cultures can be re-stimulated weekly using freshly prepared I-MVA infected and autologous PBMCs at a responder to stimulator ratio of 2:1 and supplemented with 25 IU/ml IL-2. After four cycles of re-stimulation, bulk cultures can be further tested for immune activation and many test parameters. Controls include purified virus and uninfected cells. Comparative test parameters of immune activation include cytokine production, cytotoxicity against target cells, and cell activation (including target cell death and mixed lymphocyte reaction [MLR]) using the methods described in more detail below. For these studies, ANOVA is used to statistically compare the groups.

b. Cytokine Assays

Inflammatory mediators or cytokines (e.g., TNF-α; IFN-gamma) generated by PBMCs after in vitro stimulation with I-MVA, I-MVA-infected cells, or no (control) stimulus. Cells are assayed by immunoassays of culture supernatants from multi-well plates or by ELISPOT assays in which cells are attached to plates containing an antibody against the cytokine of interest (e.g., IFN-gamma). Supernatants from stimulated PBMCs (infected cells or purified virus) are compared to control cultures (i.e., media only and uninfected cells with no stimulus) ELISA, Western or dot-blot assays can be used to compare cytokine production by cells in the test groups. Values of stimulated cells are adjusted for background and baseline values of the control groups so that induced or increased cytokine production is measured.

Cytotoxic T lymphocytes (CTLs) are also tested for their production of TNF-α or IFN-gamma following co-culture with selected lines of I-MVA-infected compared to uninfected cells. Cytokine assays may have many variables and methodologies. An example test method is as follows. Stimulator cells are infected for 4 hr with I-MVA at an MOI of 1 FFU/cell, extensively washed, and plated in 6-well plates at $8 \times 10^5$ cells/well. After an overnight incubation 12–15 hr at 37° C., Effector T cells ($5 \times 10^6$ cells/well) are added. Effector cells co-cultured with uninfected cells are used as negative reference controls. All assays are done at least in triplicate. For cytokine (e.g., TNF-α or IFN-gamma) assays, supernatants are harvested after 40 h, and the cytokine content (ng/ml) is determined by multi-well plate ELISA or ELISPOT assays (e.g., R&D Systems; Cell Systems).

c. Mixed Lymphocyte Reaction (MLR)

MLR assays may have many variables and methodologies. An example test method is as follows. "Responder" PBMCs ($1 \times 10^5$ cells/well) are seeded into 96-well culture plates. I-MVA-infected autologous PBMCs (1–3 hr pi), and mock-infected control cells are treated with mitomycin C (25 ug/ml) then added ($1 \times 10^5$ cells/well) to the responder cells (1:1 ratio). Cell proliferation is measured after 96 hrs with a BRDU ELISA assay as described above.

d. Chromium Release Assays (CRAs)

CRAs may have many variables and methodologies. An example test method is as follows. The lytic activity of either in vitro-stimulated "Effector" {E} Cytotoxic T Lymphocytes (CTLs) are tested against I-MVA-infected or uninfected Target {T} cells in a 4-hr standard $^{51}$Cr release assay. Target cells are infected for 2 h with I-MVA at an MOI of 1 FFU/cell, washed once, then labeled with 100 μCi Na$^{51}$CrO$_4$ for 1 h at 37° C. After 4 washes with PBS, labeled target cells are plated in U-bottomed 96-well plates at $1 \times 10^4$ cells/well and incubated at 37° C. At 15–18 hr after infection, effector cells are incubated with the target cells at various E: T ratios (0:1, 25:1, 50:1, 100:1). After 4 hr, the plates are centrifuged to pellet the cells, 100 μl of supernatant per well is collected, counted, and recorded as Mean+/− SD counts per minute (cpm) of replicate samples (n=4). The specific $^{51}$Cr release is determined by subtracting the background counts of cells in the 0:1 {E:T} group where there are no effector cells added. Results of the test groups are compared by ANOVA statistical analyses to determine differences between groups at a P value <0.05.

D. Manufacturing

The manufacturing steps for production of the vaccine will include the use of existing disposable cell propagation devices, connectors, and other closed system technologies that are adaptable from laboratory cell culture to scale-up manufacturing of large batches.

FIG. 15 is an example of the overall manufacturing approach from virus propagation to packaging. In this example, the MVA virus is propagated on BHK-21 cells that are cultured to high culture density on microcarrier beads in plastic cell culture bags, followed by concentration and purification of the virus, combining the virus with a proprietary oral delivery formulation as the "vaccine mixture", processing the vaccine mixture to a tablet, paste, gel, liquid or other oral delivery form, then packaging it in a foil package, blister pack, or other standard form as a single unit dose. All procedures and materials for virus propagation and handling at all steps of the manufacturing are selected with the notion that they can be scaled up from laboratory lots to 200 or more liters, then discarded after use, to remove the validation and other aspects related to cleaning and sterilization of vessels and other manufacturing components.

FIG. 16 shows examples of the types of closed and FDA approved, disposable products that will be obtained from qualified vendors and used for manufacturing steps. They include a variety of plasticware disposables that can be scaled larger manufacturing needs. FIG. 17 shows an example of how FDA Approved cGMP Components, Connectors, and Closed, Integrated Systems might be combined as a manufacturing step.

FIG. 18 shows an example of an Oravax™ sample package prepared as a unit dose package for oral delivery. The unit dose would include I-MVA in a formulation that has been tableted or is prepared as a paste or gel that can be squeezed from the foil or other packaging. The package can be made as foil or blister packages to which tablets are added or it can be made as a form, fill, seal method whereby the package is formed, filled with the vaccine product (gel, paste, liquid, then sealed in a package that can be opened for single use consumption. Features of the package are that it does not allow light or moisture and, preferably, the product can be stored at room temperature or refrigerated, but does not require freezer temperatures to maintain stability.

Manufacturing approvals and outcomes include evaluation of product: safety, potency, efficacy, stability, shelf life and other measures that include innovative and unique elements for this application. Safety of the virus lots to be used in the oral delivery formulation is tested by using appropriate human target cells, i.e., normal human cells from multiple donors and several regions of the alimentary tract. Potency is measured by determining that the vaccine virus lot is infectious for permissive cells with a quantified titer as determined by immunoplaque or other assay. Efficacy is measured by the production of protective immunity, such as virus neutralization with associated lack of infectivity for the host target cells or animals, following oral delivery of the vaccine with the immunizing virus strain included in a formulation that protects the virus and augments immune responsiveness, and has stability and a shelf life of at least a year, with preferable storage at room temperature.

Said formulation may include gelatin, cellulose, or a variety of other excipients as ingredients, or the formulation may be a gel or a food carrier such as a pudding or similar formulation that would include the virus as a component. As another embodiment flavorings, emulsifiers, or other additives may be included in the formulation of the product, the delivery vehicle or other components of the packaged material. The I-MVA immunogen can be packaged as a solution, as single doses, as a paste or gel, or in a food or nutritional substance in a plastic container, pillow-pack, tear-pack, straw tube packaging or other suitable packaging for the liquid, gel or food carrier formulation.

D. Literature Cited

1. Kortepeter, M. and G. Parker, *Potential biological weapons threats.* Emerg Infect Dis, 1999. 5: p. 523–7.
2. Henderson, D., *Looming threat of bioterrorism*. Science, 1999. 283: p. 1279–82.
3. Fenner, F., et al., *Smallpox and its eradication*. 1988, Geneva: World Health Organization.
4. Cohen, J., *Smallpox vaccinations: How much protection remains*? Science, 2001. 294: p. 985.
5. Littaua, R., et al., *Vaccinia virus-specific human CD4+ cytotoxic T-lymphocyte clones*. J Virol, 1992. 66(4): p. 2274–2280.
6. Demkowicz Jr, W., et al., *Human cytotoxic T-cell memory: Long-lived responses to vaccinia virus*. J Virol, 1996. 70(4): p. 2627–2631.
7. Demkowicz Jr, W. and F. Ennis, *Vaccinia virus-specific CD8+ cytotoxic T lymphocytes in humans*. J Virol, 1993. 67(3): p. 1538–1544.
8. Stienlauf, S., et al., *Kinetics of formation of neutralizing antibodies against vaccinia virus following re-vaccination*. Vaccine, 1999. 17(3): p. 201–4.
9. Paoletti, E., et al., *Highly attenuated poxvirus vectors: NYVAC, ALVAC and TROVAC*. Dev Biol Stand, 1995. 84: p. 159–63.
10. Moss, B., *Genetically engineered poxviruses for recombinant gene expression, vaccination, and safety*. Proc Natl Acad Sci USA, 1996. 93: p. 11341–11348.
11. Mayr, A., V. Hochstein-Mintzel, and H. Stickl, *Abstammung, Eigenschaften, und Verwendung des attenuierten Vaccinia-Stammes MVA*. Infection, 1975. 3: p. 6–14.
12. Meyer, H., G. Sutter, and A. Mayr, *Mapping of deletions in the genome of the highly attenuated vaccinia virus MVA and their influence on virulence*. J Gen Virol, 1991. 72: p. 1031–1038.
13. Sutter, G., et al., *A recombinant vector derived from the host range-restricted and highly attenuated MVA strain of vaccinia virus stimulates protective immunity in mice to influenza virus*. Vaccine, 1994. 12: p. 1032–1040.
14. Sutter, G., et al., *Stable expression of the vaccinia virus K1L gene in rabbit cells complements the host range defect of a vaccinia virus mutant*. J Virol, 1994. 68: p. 4109–4116.
15. Drexler, I., et al., *Highly attenuated modified vaccinia virus Ankara replicates in baby hamster kidney cells, a potential host for virus propagation, but not in various human transformed and primary cells*. J Gen Virol, 1998. 79: p. 347–352.
16. Konetschny, C., G. Holzer, and F. Falkner, *Retroviral vectors produced in the cytoplasmic vaccinia virus system transduce intron-containing genes*. J Virol, 2002. 76(3): p. 1236–43.
17. Schneider, J., et al., *Enhanced immunogenicity for CD8+ T cell induction and complete protective efficacy of malaria DNA vaccination by boosting with modified vaccinia virus Ankara*. Nat Med, 1998. 4: p. 397–402.
18. Drexler, I., et al., *Modified vaccinia virus Ankara for delivery of human tyrosinase as melanoma-associated antigen: Induction of tyrosinase-and melanoma-specific human leukocyte antigen A *0201-restricted cytotoxic T cells in vitro and in vivo*. Cancer Res, 1999. 59: p. 4955–4962.
19. Carroll, M., et al., *Highly attenuated modified vaccinia virus Ankara (MVA) as an effective recombinant vector: a murine tumor model*. Vaccine, 1997. 15: p. 387–394.
20. Nam, J., et al., *Protection against lethal Japanese encephalitis virus infection of mice by immunization with the highly attenuated MVA strain of vaccinia virus expressing JEV prM and E genes*. Vaccine, 1999. 17: p. 261–268.
21. Sutter, G. and B. Moss, *Nonreplicating vaccinia vector efficiently expresses recombinant genes*. Proc Natl Acad Sci USA, 1992. 89: p. 10847–10851.
22. Hochstein-Mintzel, V., H. Huber, and H. Stickl, *Oral and nasal immunization with poxvirus vaccinae 3rd communication: animal experiments*. Zentralb Bacteriol, 1972. 15: p. 30–96.
23. Mayr, A. and K. Danner, Berl Munch Tierarztl Wochenschr, 1979. 92: p. 251.
24. Mayr, A., et al., *Smallpox vaccination strain MVA: marker, genetic structure, experience gained with the parenteral vaccination and behavior in organisms with a debiliated defense mechanism*. Zbl Bakt Hyg; I Abt Org B, 1978. 167: p. 375–390.
25. Meitin, C., B. Bender, and P. Small Jr., *Influenza immunization: intranasal live vaccinia recombinant contrasted with parenteral inactivated vaccine*. Vaccine, 1991. 9: p. 751–756.
26. Stickl, H., Dtsch Med Wochenschr, 1974. 99: p. 2386.
27. Hirsch, V., et al., *Patterns of viral replication correlate with outcome in simian immunodeficiency virus (SIV)-infected macaques: effect of prior immunization with a trivalent SIV vaccine in modified vaccinia virus Ankara*. J Virol, 1996. 70: p. 3741–3752.
28. Gomez, C., et al., *Enhanced CD8(+) T cell immune response against a V3 loop multi-epitope polypeptide (TAB13) of HIV-1 Env after priming with purified fusion protein and booster with modified vaccinia virus Ankara (MVA-TAB) recombinant: a comparison of humoral and cellular immune responses with the vaccinia virus Western Reserve (WR) vector*. Vaccine, 2001. 20: p. 961–971.
29. Larsson, M., et al., *Efficiency of cross presentation of vaccinia virus-derived antigens by human dendritic cells*. Eur J Immunol, 2001. 31(12): p. 3432–42.
30. Tartaglia, J., et al., *Live vectors as vaccines: highly attenuated poxvirus vectors*. AIDS Res Hum Retroviruses, 1992. 8: p. 1445–7.
31. Wee, E.-T., et al., *A DNA/MVA-based candidate human immunodeficiency virus vaccine for Kenya induces multi-specific T cell responses in rhesus macaques*. J Gen Virol, 2002. 83: p. 75–80.
32. Werner, G., et al., *Studies on poxvirus infections in irradiated animals*. Arch Virol, 1980.64: p. 247–256.
33. Sharpe, S., et al., *Induction of simian immunodeficiency virus (SIV)-specific CTL in rhesus macaques by vaccination with modified vaccinia virus Ankara expressing SIV transgenes: influence of pre-existing anti-vector immunity*. J Gen Virol, 2001. 82: p. 2215–2223.
34. Belyakov, I., et al., *Mucosal vaccination overcomes the barrier to recombinant vaccinia immunization caused by preexisting poxvirus immunity*. Proc Natl Acad Sci USA, 1999.96: p. 4512–4517.
35. Cross, R., C. Kaplan, and D. McClean, Lancet, 1957. 1: p. 446.

36. Moyer, M. and H. Gendelman, *HIV replication and persistence in human gastrointestinal cells cultured in vitro*. J Leukocyte Biol, 1991. 49: p. 499–504.
37. Moyer, M., *Culture of human gastrointestinal epithelial cells*. Proc Soc Exp Biol Med, 1983. 174: p. 12–15.
38. West, B., A. Isaac, and et al., *Localization of villin, a cytoskeletal protein specific to microvilli, in human ileum and colon and in colonic neoplasms*. Gastroenterology, 1988.94: p. 343–352.
39. Frey S. E., F. K. Newman, J. Cruz, B. Shelton B., J. M. Tennant et al. *Dose Related Effects of smallpox Vaccine*. N Eng J Med 2002, 346: p.1275–80.
40. Frey S. E., R. B. Couch., C. O Tacket, J. J. Treanor, M. Wolff, F. K. Newman et al. *Clinical Responses to Undiluted and Diluted Smallpox Vaccine*. N Eng J Med 2002, 346: p.1265–74.

What is claimed is:

1. An oral vaccine comprising:
a replication-defective or deficient vaccinia virus, or a modified vaccinia virus strain that is unable to generate infectious virus in human cells but is able to replicate in an animal host cell which is permissive for the virus, in a formulation comprising hydroxyethyl starch, mannitol, nutritional supplement grade fish oil, glycerol, and gelatin;

wherein gel-sol virus carrier excipient components comprising a mixture of equal parts of microcrystalline cellulose and guar gum; water-dispersible microcrystalline cellulose containing sodium carboxymethylcellulose (NaCMC); and internally cross-linked, water-insoluble sodium carboxymethylcellulose (NaCMC) is added to the formulation to form a paste or gel for oral delivery.

2. The oral vaccine of claim 1, wherein the formulation comprises 6% (w/v) hydroxyethyl starch, 40% (v/v) mannitol, 0.15% (v/v) nutritional supplement grade fish oil, 5% (v/v) glycerol, 0.5% (w/v) gelatin.

3. The oral vaccine of claim 2, wherein the gel-sol virus carrier excipient components are added to said formulation to final concentration of 10% (w/v).

4. The oral vaccine of claim 1, wherein the strain of virus is MVA.

5. The vaccine of claim 1, wherein said virus is provided in the range of $5\times10^4$ to $2\times10^8$ infectious FFU.

6. The vaccine of claim 5, wherein said virus is provided in a range of $1\times10^6$ to $1\times10^8$ infectious FFU.

7. The vaccine of claim 1, wherein the vaccine is packaged in a unit dose form.

8. A formulation for oral delivery of a vaccinia virus to immunize an animal or human subject, comprising hydroxyethyl starch, mannitol, nutritional supplement grade fish oil, glycerol, and gelatin, wherein a mixture of equal parts of microcrystalline cellulose and guar gum; water-dispersible microcrystalline cellulose containing sodium carboxymethylcellulose (NaCMC); and internally cross-linked, water-insoluble sodium carboxymethylcellulose (NaCMC) is added to the formulation to form a paste or gel for oral delivery.

9. The formulation of claim 8, comprising 6% (w/v) hydroxyethyl starch, 40% (v/v) mannitol, 0.15% (v/v) nutritional supplement grade fish oil, 5% (v/v) glycerol, 0.5% (w/v) gelatin, wherein a mixture of equal parts of microcrystalline cellulose and guar gum; water-dispersible microcrystalline cellulose containing sodium carboxymethylcellulose (NaCMC); and internally cross-linked, water-insoluble sodium carboxymethylcellulose (NaCMC) is added to said formulation to a final concentration of 10% (w/v).

10. A method for immunizing a mammal against vaccinia virus, comprising orally administering an effective dose of a replication-defective or deficient vaccinia virus, or a modified vaccinia virus strain that is unable to generate infectious virus in human cells but is able to replicate in an animal host cell which is permissive for the virus, in a paste or gel formulation comprising hydroxyethyl starch, mannitol, nutritional supplement grade fish oil, glycerol, and gelatin, wherein a mixture of equal parts of microcrystalline and guar gum; water-dispersible microcrystalline cellulose containing sodium carboxymethylcellulose (NaCMC); and internally cross-linked, water-insoluble sodium carboxymethylcellulose (NaCMC) is added to the formulation to form a paste or gel for oral delivery.

11. The method of claim 10, wherein said formulation comprises 6% (w/v) hydroxyethyl starch, 40% (v/v) mannitol 0.15% (v/v) nutritional supplement grade fish oil, 5% (v/v) glycerol, 0.5% (w/v) gelatin, and wherein a mixture of equal parts of microcrystalline cellulose and guar gum; water-dispersible microcrystalline cellulose containing sodium carboxymethylcellulose (NaCMC); and internally cross-linked, water-insoluble sodium, carboxymethylcellulose (NaCMC) is added to said formulation to final concentration of 10% (w/v).

12. The method of claim 10, wherein said virus is delivered into the alimentary tract as whole virions that are taken up at multiple sites in the tract and into the host circulation to stimulate host immunity.

13. The method of claim 12, wherein two of said sites are the oral cavity and the small intestine.

14. The method of claim 10, wherein the immune response is a systemic response.

15. The method of claim 10, wherein the immune response is a mucosal response.

16. The method of claim 10, wherein the immune response includes humoral and cell-mediated immunity.

17. The method of claim 10, wherein both a systemic and mucosal response is produced.

18. The method of claim 10, wherein said virus is provided in a range of $5\times10^4$ to $2\times10^8$ infectious FFU.

19. The method of claim 18, wherein said virus is provided in a range of $1\times10^6$ to $1\times10^8$ infectious FFU.

20. The method of claim 10, wherein said strain of virus is MVA.

21. The method of claim 10, wherein in the formulation is dried and delivered in tablet form.

22. The method of claim 10, further comprising one or more booster immunizations.

23. An oral vaccine comprising:

a replication-defective or deficient vaccinia virus, or a modified virus that is unable to generate infectious virus in human cells but is able to replicate in an animal host cell which is permissive for the virus, in a formulation comprising hydroxyethyl starch, mannitol, nutritional supplement grade fish oil, glycerol, and gelatin, wherein gel-sol virus carrier excipient components comprising a mixture of equal parts of microcrystalline cellulose and guar gum; water-dispersible microcrystalline cellulose containing sodium carboxymethylcellulose (NaCMC); and internally cross-linked, water-insoluble sodium carboxymethylcellulose (NaCMC) is added to the formulation to form a paste or gel for oral delivery; and wherein said vaccine is effective in protecting an animal against a lethal challenge with an infectious strain of vaccinia virus.

24. An oral vaccine comprising:

$5 \times 10^4$ to $2 \times 10^8$ infectious FFU of MVA in a formulation comprising 6% (w/v) hydroxyethyl starch, 40% (v/v) mannitol, 0.15% (v/v) nutritional supplement grade fish oil, 5% (v/v) glycerol, 0.5% (w/v) gelatin, and wherein a mixture of equal parts of microcrystalline cellulose and guar gum; water-dispersible microcrystalline cellulose containing sodium carboxymethylcellulose (NaCMC); and internally cross-linked, water-insoluble sodium carboxymethylcellulose (NaCMC) is added to said formulation to final concentration of 10% (w/v).

25. The oral vaccine of claim 24, wherein $1 \times 10^6$ to $1 \times 10^8$ infectious FFU of MVA are present in said vaccine formulation.

* * * * *